US009763822B2

(12) United States Patent
Pelaez

(10) Patent No.: US 9,763,822 B2
(45) Date of Patent: Sep. 19, 2017

(54) UPPER TORSO HARNESS WITH DETACHABLE NECK, CHIN AND HEAD COVERING OR SCARF

(71) Applicant: Martin Pelaez, Las Vegas, NV (US)

(72) Inventor: Martin Pelaez, Las Vegas, NV (US)

( * ) Notice: Subject to any disclaimer, the term of this patent is extended or adjusted under 35 U.S.C. 154(b) by 305 days.

(21) Appl. No.: 14/617,521

(22) Filed: Feb. 9, 2015

(65) Prior Publication Data
US 2015/0272769 A1 Oct. 1, 2015

Related U.S. Application Data

(60) Provisional application No. 61/971,025, filed on Mar. 27, 2014.

(51) Int. Cl.
A61F 5/02 (2006.01)
A61F 5/055 (2006.01)

(52) U.S. Cl.
CPC ............. A61F 5/02 (2013.01); A61F 5/055 (2013.01)

(58) Field of Classification Search
CPC . A62B 35/04; A62B 35/0068; A62B 35/0018; A62B 35/0037; E04G 21/3261
See application file for complete search history.

(56) References Cited

U.S. PATENT DOCUMENTS 6,367,582 B1 * 4/2002 Derby ................ A62B 35/0018
119/857
6,804,830 B2 10/2004 Reynolds et al.
7,086,091 B2 8/2006 Jordan
8,522,918 B1 9/2013 Al-Wasis
8,651,234 B2 2/2014 Yocco
2012/0260386 A1 10/2012 Overbeeke
2013/0160180 A1 6/2013 Carcich et al.
2013/0175117 A1 7/2013 Schierenbeck
2013/0175118 A1 7/2013 McDonald et al.
2013/0192923 A1 8/2013 Kennedy
2013/0319793 A1* 12/2013 Stibilj ................ A62B 35/0012
182/3

FOREIGN PATENT DOCUMENTS

WO WO9913947 3/1999

* cited by examiner

Primary Examiner — Ophelia A Hawthorne
(74) Attorney, Agent, or Firm — Weiss & Moy, P.C.; Veronica-Adele R. Cao

(57) ABSTRACT

A garment and device generally designated as an upper torso compression and support harness with a detachable neck, chin and head covering or scarf. The scarf fabric is of similar construction to common turtle necks, but is connected to the harness via multiple connection methods, including, but not limited to buttons, VELCRO hook and loop fasteners, or sewing attachment. Specifically, the present invention consisting of lightweight compression and elastic fabric bands of a certain width, configured in a comfortable and efficient pattern to enable compression assistance to the participant and a secure attachment point for a scarf of head covering. The present invention also envisions design elements to provide locations to affix team insignias, sponsor marks and logos, and additional means of customization. The harness straps cross the upper torso in an X-shaped pattern with lateral support straps running down the length of the torso.

11 Claims, 10 Drawing Sheets

UPPER TORSO HARNESS WITH DETACHABLE NECK, CHIN AND HEAD COVERING OR SCARF

CROSS REFERENCE TO RELATED APPLICATION

This non-provisional application claims priority to U.S. Provisional Application No. 61/971,025 filed on Mar. 27, 2014 in the name of the Applicant herein.

FIELD OF THE INVENTION

The present invention relates generally to a component of sports paraphernalia or clothing and specifically to a primary component of a detachable neck, chin and lower head covering for warmth and protection from the elements. The harness portion of the present invention is designed to safely support a participant's torso without extra or burdensome fabric, thereby reducing drag but providing the participant with muscle and compression support. The detachable neck, chin and lower head covering is designed to increase the comfort of the participant when the conditions warrant additional protection or warmth in that body region. Additional benefits of aesthetics are also designed into the present invention such as customized participant numbers, names, team insignias and logos, and sponsors in various locations on the harness and detachable covering.

BACKGROUND OF THE INVENTION

The present invention relates to an upper torso harness, specifically to provide stability and compression resistance to the participant of a sporting activity. The present invention allows the user to connect a protective scarf or fabric sleeve to the harness and adjust the protection and covering to encompass the neck, chin and lower head.

Compression harnesses are used for a variety of recreation and commercial purposes. Recreational uses include mountain climbing and exploration of caves, while commercial purposes may include high-rise window washing and emergency service rescues. A great variety of harnesses exist in the marketplace. Some harnesses, particularly those used for commercial purposes, may be full-body harnesses, which include shoulder and chest straps as well as a waist band and leg loops. Other harnesses may have only a simple waist band such as might be worn as a safety harness by a person participating in climbing wall activities.

A compression harness used in the method of the present invention is a new and novel approach to be used in a variety of environments. Sports enthusiasts and participants may wear the present invention for purely aesthetic reasons, while other participants may utilize the present invention to offer additional support to muscle tension and responsiveness.

The primary purpose of any harness, whether for recreation or commercial use, is to prevent gravity from having an adverse effect on the climber or user. However, this present invention, classified as a harness, makes no claim to prevent or support the forces of gravity from asserting itself on the participant and user. As such, this harness is focused on providing compression support and certain aesthetics to the user.

Known harnesses provide for a number of adjustments to allow the user to fit the harness to the participant's body. While a number of harnesses are known which have adjustable leg loops, wherein the girth of the leg loop may be adjusted about the user's thigh, known harnesses do not allow for the adjustment of the rise, which, as used herein in the case of a climbing harness, is the distance between the waistband and the leg loops. Additionally, a full body harness may have similar adjustable loops for chest, head and arm insertion. The previously known solution to this problem has been to provide leg loops which are detachable from a waist band, and for manufacturers to provide the leg loop assembly in a variety of sizes. However, the current invention looks toward comfort and neck protection from the elements, allowing the scarf covering to stay in place without the need for a bulky additional shirt or protective torso covering.

Similarly, there are other performance garments and apparel that provide users and participants with neck and head coverings. However, these options and apparel do not provide a solution for the drag and uncomfortable fit of an additional shirt or apparel covering on the participant's torso.

U.S. Patent Application No.: 1998/018039 (PCT/US1998/018039) (WO01999013947) relates to an invention that provides a full body harness which utilizes a reduced number of components thereby simplifying construction and reducing manufacturing costs. The harness has only four pieces of webbing, two identical shoulder straps and two identical leg straps. These shoulder straps and leg straps are connected to two uniquely designed, multi-functional hip plates. The harness also has a standard back pad and a standard shoulder strap retainer. While the publication discloses a system and harness that may provide additional protection from a fall or a climbing accident, it does not address the needs the present invention undertakes. There is no option for a detachable scarf or head covering, no intended location for a team logo or crest on the harness, and compression fabric integrated in the design.

U.S. Publication No.: 2013/0192923 relates to an apparatus so designed that when properly used may aid in the prevention of injury and or even death. This device is so designed that a fallen hunter is left hanging facing the tree, allowing mobility and movement. With the attached (DOWN E-Z) device, one may lower himself to the ground with little or no effort. This final step is very important due to the documented factual records of hunters dying while being left hanging for hours and blood begins to clot. This publication discloses a safety harness used mostly by tree stand Hunters with a Descender attachment for self-controlled lowering one's self to the ground in case of an accidental fall. However, the present invention does not act as harness for descending heights, but rather acts as a support and compression harness for athletic activity to provide compression support and protection from cold and other elements for the head, chin and neck areas of the body.

U.S. patent application Ser. No. 13/347,386 (U.S. Publication No. 2013/0175117) relates to an upper body harness portion for converting a seat-style harness to a full body harness. The upper body harness portion includes a front lower component, a rear lower component, and an upper torso component having elongated first, second and third webbings. The ends of the first and second webbings are detachably securable to opposite sides of the front and rear or side portions of the seat-style harness waist belt, respectively. The third webbing forms a closed loop which, when worn, extends over a wearer's shoulders on opposite sides of the wearer's head. First and second connectors are slidably connected to the third webbing, with the first connector also being slidably connected to the first webbing adjacent the front of a wearer and the second connector being slidably connected to the second webbing adjacent the back of a wearer. The publication does not disclose a detachable head and neck scarf as does the present invention. The publication is focused on securing the lower torso with optional upper torso straps. This is a distinction from the present invention, which only considers upper torso and chest harness elements.

U.S. Pat. No. 8,522,918 relates to a rescue harness that is a personal use device for donning by an individual requiring escape from an elevated location in a building structure or the like. The harness includes a front latch and bracket having a removable combination glass cutter and hammer, and a removable explosive charge. A rope brake is also secured to the bracket, and a rope passes through the brake. The user of the harness removes the glass cutter and hammer combination, and scribes an opening on a glass window panel. The explosive charge is placed on the glass in the scribed area. A timer permits the user to momentarily leave the immediate vicinity. The hammer is used to break out any remaining glass shards after the explosion blows out the scribed area of glass. The user exits the structure through the hole in the panel, using the rope brake to control his or her descent. The present invention, however, does not act as harness for descending heights, but rather acts as a support and compression harness for athletic activity with a detachable head and neck scarf.

U.S. patent application Ser. No. 13/175,982 (U.S. Publication No. 20120260386) relates to a suit that includes a hard upper torso having a visor and providing an entry opening and shoulder apertures. An interface includes a harness supporting a load plate. The harness is configured to be secured to a subject. A primary life support system is mounted to the hard upper torso and the primary life support system in a donned condition. A method of donning the suit is provided, which includes donning a harness that supports a load plate. A hard upper torso includes an entry opening through which the suit is entered. The load plate is positioned relative to the hard upper torso. A primary life support system is closed over the load plate to secure the primary life support system relative to the hard upper torso. The publication discloses an invention that focuses on supporting the torso when the user is carrying a load rather than compression and warmth as provided by the present invention. Furthermore, the two inventions are dissimilar due to the integration of a lower torso elements, which is not a functional element of the present invention.

U.S. patent application Ser. No. 13/472,875 (U.S. Pat. No. 8,651,234) also relates to a device that includes a strap having first and second opposite ends. The strap defines first and second arm loop portions positionable about corresponding shoulders of the individual and being movable between a first open configuration allowing a corresponding shoulder to be positioned therein and a second configuration for capturing the corresponding shoulder to be positioned. The strap further defines first and second leg loop portions selectively receivable about legs of the wearer and adjustable via an adjustment mechanism to tighten the leg loop portions around the wearer's legs. A connection point defined by the first and second ends of the belt is operatively connected to the strap and is positionable about a waist of the individual. The publication does not disclose support via compression or a detachable head and neck scarf for warmth. The publication discloses an invention that focuses on a tightening mechanism based on the users weight. The present invention only considers compression of the upper torso, not the users weight or lower torso.

U.S. Pat. No. 7,086,091 relates to a full-body harness, with or without an integral support line, with the harness being adaptable for class I, class II, and/or class III service, and for use by safety personnel, such as firefighters, for example, for situations that call for emergency activity in areas where falls from an unsafe height are possible. This publication discloses an invention that provides support to a descending user from a certain height, while the present inventions intent is to provide compression support, warmth, and style in a minimal design for ease of use for the participant in an athletic activity.

U.S. Pat. No. 6,804,830 relates to a full body harness which can include curved webbing, a spreading back pad and/or leg buckles which improve the comfort, use and performance of the harness. Preferably, the harness uses five pieces of webbing, namely, two curved webbing shoulder straps, two identical leg straps, and a sub-pelvic strap. The harness can also have a spreading back pad which helps to keep the shoulder straps from riding up onto the neck of the wearer. Once again, the publication discloses an invention that provides support to a descending user from a certain height, while the present invention provides compression support, warmth, and style in a minimal design for ease of use for the participant in an athletic activity.

U.S. patent application Ser. No. 13/507,588 (U.S. Publication No. 2013/0175118) relates to a full-body safety harness that is to be worn by a user, especially a user in a hostile environment. Which such full body safety harness comprises a torso surrounding portion with a D-ring for attaching a life line, two vertical shoulder straps, four straps that affixes to a pair of pants, and two leg supporting straps that clip around the legs. All portions of this safety harness extend over a portion of a person's body to retain the person within the full-body safety harness. The straps of this full-body safety harness are fabricated from a flexible material having an elastic extension in the range of 10%-25% under a tension load of approximately 100 newtons. This percentage of stretch of this full-body safety harness is controlled by additional static material that is stitched onto the straps in a controlled loop pattern. Yet again the publication discloses an a harness that provides support to a descending user from a certain height, while the present invention provides compression support, warmth, and style in a minimal design for ease of use for the participant in an athletic activity.

U.S. Publication No.: 2013/0160180 relates to the difficulty of an athlete to maintain comfortable overall body temperature, during different periods of exercise which result in variations of body temperature, by providing a garment of variable configuration and permeability. The garment of the invention includes a torso portion and a turtleneck portion. The turtleneck portion extends from the torso portion. The turtleneck portion includes a first panel made of a first material and a second panel made of a second material. The second material is more permeable than the first material. While the publication discloses a garment that may provide additional protection and warmth from the elements, it does not address the needs the present invention addresses regarding minimal design and fabric to hinder an athletic participant. Further, there is no option for a detachable scarf or head covering, no intended location for a team logo or crest on the harness, and compression fabric integrated in the design.

As such and in conclusion, insofar as the data represents and the research concludes, there is no harness option that provides a detachable scarf or neck and head covering to be used in athletic activity. The prior art discussion above does not disclose a product, or application or invention that is within the patent registry that fulfills all elements the present invention claims.

SUMMARY OF THE INVENTION

This summary is provided to introduce a selection of concepts in a simplified form that are further described below in the DESCRIPTION OF THE INVENTION. This summary is not intended to identify key features of the claimed subject matter, nor is it intended to be used as an aid in determining the scope of the claimed subject matter.

The present invention is a garment comprising an upper torso harness with a detachable neck, chin and head covering or scarf. Similar descriptions classify the fabric covering as a "Turtle Neck" which is connected to the harness via multiple connection methods, including, but not limited to buttons, zippers, VELCRO, or sewing attachment. Specifically, the present invention consisting of lightweight elastic straps of a certain width, configured in a comfortable and efficient pattern to enable compression support to the participant and a secure attachment point for a scarf of head covering. The present invention also envisions design elements to provide locations to affix team insignias, sponsor marks and logos, and additional means of customization. The support compression straps cross the upper torso in an "X" pattern with lateral support straps running down the length of the torso. All the fabric used in the compression straps and the head and neck scarf is high-tech, flexible, temperature controlling, and breathable material to provide comfort and support to the athletic user.

In accordance with one embodiment of the present invention, a garment is disclosed. The garment comprises: A garment comprising: a plurality of straps positioned around an upper torso of a user, the straps defining a plurality of open areas therebetween; and a neck covering removably coupled to the straps.

In accordance with another embodiment of the present invention, a garment is disclosed. The garment comprises: a harness positioned around an upper torso of a user, wherein the harness comprises: a left shoulder strap; a right shoulder strap; a front left lateral support strap and a rear left lateral support strap coupled to and extending downwardly from the left shoulder strap; a front right lateral support strap and a rear right lateral support strap coupled to and extending downwardly from the right shoulder strap; a front left compression strap and a rear left compression strap coupled to and extending diagonally and downwardly from the left shoulder strap, wherein the front left compression strap is adapted to extend across the upper torso of the user and couple to the front right lateral support strap and wherein the rear left compression strap is adapted to extend across the upper torso of the user and couple to the rear right lateral support strap; a front right compression strap and a rear right compression strap coupled to and extending diagonally and downwardly from the right shoulder strap, wherein the front right compression strap is adapted to extend across the upper torso of the user and couple to the front left lateral support strap and wherein the rear right compression strap is adapted to extend across the upper torso of the user and couple to the rear left lateral support strap; and a front patch coupled to the front left compression strap and to the front right compression strap, wherein the front patch bears at least one indicia that is adapted to identify the user. The garment also has a neck covering removably coupled to the harness, wherein the neck covering has an open bottom and an open top and is adapted to receive a head of the user therethrough.

In accordance with another embodiment of the present invention, an athletic garment is disclosed. The athletic garment comprises: a harness positioned around an upper torso of a user, wherein the harness comprises: a left shoulder strap; a right shoulder strap; a front left lateral support strap and a rear left lateral support strap coupled to and extending downwardly from a lateral end of the left shoulder strap; a front right lateral support strap and a rear right lateral support strap coupled to and extending downwardly from a lateral end of the right shoulder strap; a front patch adapted to be positioned over a center of a chest of the user, wherein the front patch bears at least one indicia that is adapted to identify the user; a rear patch adapted to be positioned over a center of a back of the user, wherein the rear patch bears at least one indicia that is adapted to identify the user; a front left upper compression strap coupled at one end to the lateral end of the left shoulder strap and coupled at an opposite end to the front patch; a front right lower compression strap coupled at one end to the front patch and coupled at an opposite end to a distal end of the front right lateral support strap; a front right upper compression strap coupled at one end to the right shoulder strap and coupled at an opposite end to the front patch; a front left lower compression strap coupled at one end to the front patch and coupled at an opposite end to the front left lateral support strap; a rear left upper compression strap coupled at one end to the left shoulder strap and coupled at an opposite end to the rear patch; a rear right lower compression strap coupled at one end to the rear patch and coupled at an opposite end to the rear right lateral support strap; a rear right upper compression strap coupled at one end to the right shoulder strap and coupled at an opposite end to the rear patch; and a rear left lower compression strap coupled at one end to the rear patch and coupled at an opposite end to the rear left lateral support strap; and a neck covering removably coupled to the harness, wherein the neck covering has an open bottom and an open top and is adapted to receive a head of the user therethrough, and wherein the neck covering bears at least one indicia that is adapted to identify the user; and a plurality of clasps, wherein one clasp is coupled to and extends downwardly from each of front left lateral support strap, the front right lateral support strap, the rear left lateral support strap, and the rear right lateral support strap and wherein the clasps are adapted to removably couple the harness to another article of clothing of the user; and wherein the harness defines a plurality of open areas in the garment.

BRIEF DESCRIPTION OF THE DRAWINGS

Other features, functionality, and advantages of the present invention will become more apparent from the following detailed description of the method and its derivatives and certain modifications thereof when taken together with the accompanying drawings in which.

DETAILED DESCRIPTION OF THE PREFERRED EMBODIMENTS

Figure 1:
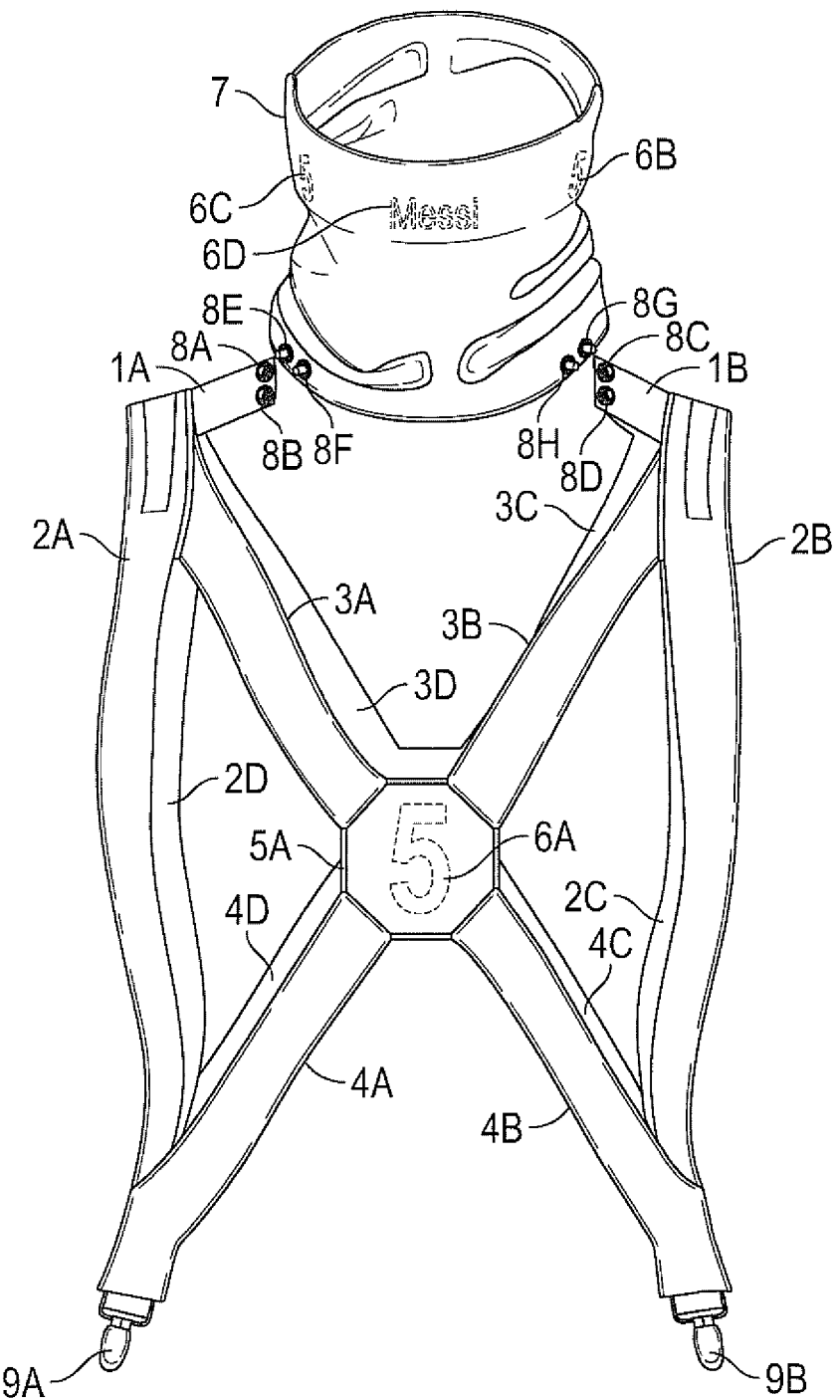
FIG. 1 is a front view of the garment of the present invention depicting the layout and articulation of the harness straps placement and location. Additionally, this figure depicts the location of number insignias of the player, and the location of the head and neck covering articulation to the harness via a connection method.

The present invention will be described in detail with reference to embodiments thereof as illustrated in the accompanying drawings and figures, in which like reference numerals are used to indicate identical or functionally similar elements. References to "one embodiment", "an embodiment", "an example embodiment", etc., indicate that the embodiment described may include a particular feature, structure, or characteristic, that every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The following examples are illustrative, but not limiting, of the present invention. Other suitable modifications and adaptations of the variety of conditions and parameters normally encountered in the field, and which would be apparent to those skilled in the art, are within the spirit and scope of the invention.

Figure 2:
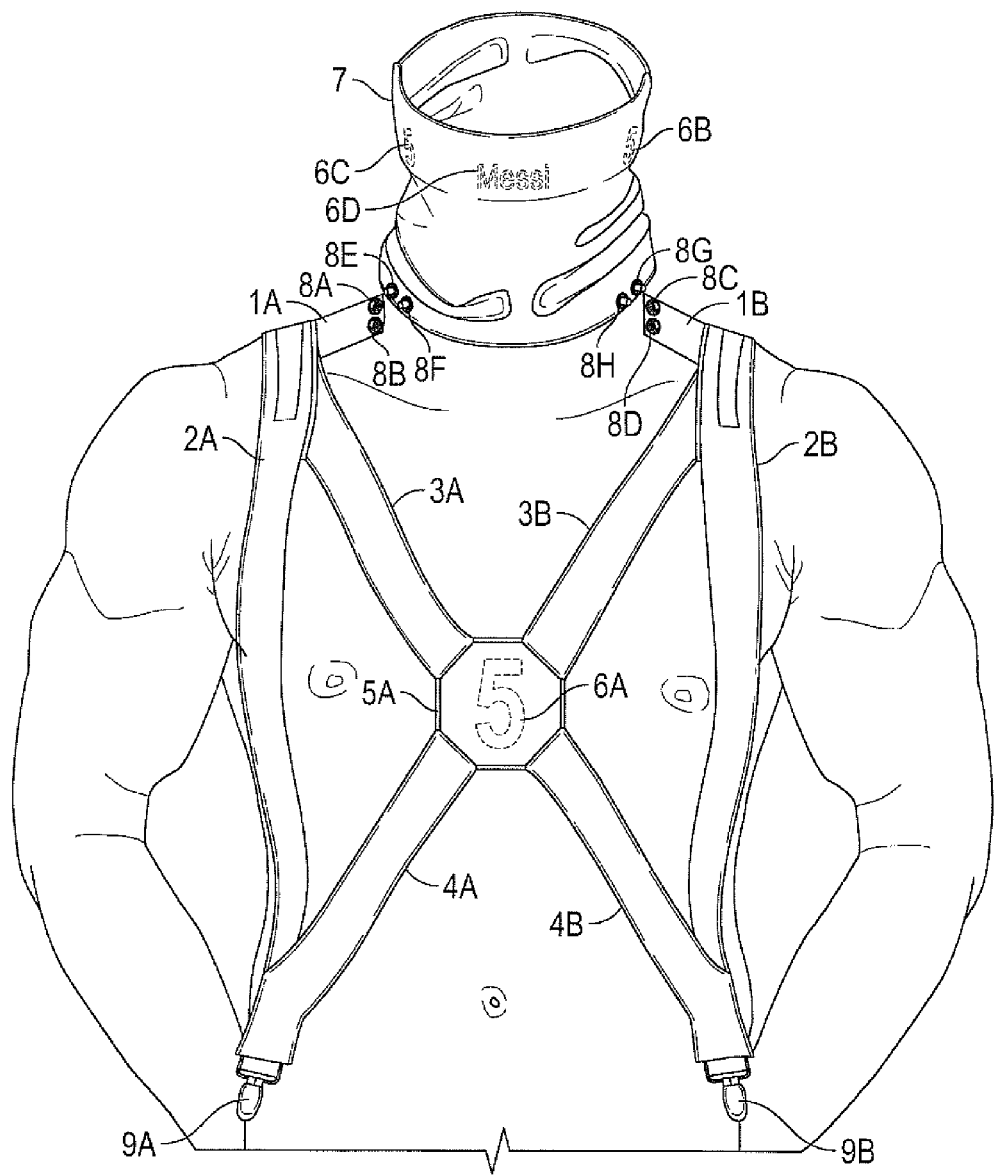
FIG. 2 is a front view of the harness of FIG. 1, shown as worn by a user.

FIGS. 1-2 show a front view of the present invention depicting the layout and articulation of the garment 10. The garment 10, in its simplest form, comprises a harness 100 and a detachable neck covering or scarf 7. The harness 100 may have: two shoulder straps 1A, 1B and a plurality of front harness straps 2A, 2B, 3A, 3B, 4A, 4B; a plurality of rear harness straps 2C, 2D, 3C, 3D, 4C, 4D. The straps 1A, 1B, 2A, 2B, 2C, 2D, 3A, 3B, 3C, 3D, 4A, 4B, 4C, 4D together define a plurality of open areas 200. These open areas 200 provide openings for the user's head and arms, and also contribute to the simplicity and breathability of the garment 10. The shoulder straps may comprise a right shoulder strap 1A and a left shoulder strap 1B. The front harness straps may comprise: a front right upper compression strap portion 3A and a front left upper compression strap portion 3B; a front right lower compression strap portion 4A and a front left lower compression strap portion 4B; a front right lateral support strap 2A and a front left lateral support strap 2B. The front right upper compression strap 3A may be coupled at one end to a lateral end of the right shoulder strap 1A, extend across a portion of the upper torso of the user, and be coupled at another end to a front patch 5A. The front left lower compression strap 4B may be coupled at one end to the front patch 5A, extend across the remaining portion of the upper torso of the user, and be coupled at another end to a distal end of the front left lateral support strap 2B. The front left upper compression strap 3B may be coupled at one end to a lateral end of the left shoulder strap 1B, extend across a portion of the upper torso of the user, and be coupled at another end to the front patch 5A. The front right lower compression strap 4A may be coupled at one end to the front patch 5A, extend across the remaining portion of the upper torso of the user, and be coupled at another end to a distal end of the front right lateral support strap 2A. In the embodiment shown, the patch 5A may be in the shape of an octagon, thereby providing a plurality of flat edges to which the front right upper compression strap 3A, front left lower compression strap 4B, front left upper compression strap 3B, and front right lower compression strap 4A may be coupled.

The harness 100 may also have a detachable scarf 7, or other suitable neck covering, coupled to the two shoulder straps 1A, 1B. The scarf 7 may be adapted to cover not only the neck, but also the chin and head of the user. The figures herein describe a scarf 7 that has an open top, but it should be clearly understood that substantial benefit may still be derived from the use of a scarf 7 that also covers the entire head of the user (similar to a ski mask). The scarf 7 may be made from various elastic fabric to enable warmth and support to the user, in addition to uniform construction without seams to allow an expandable opening for the players head to pass through. The scarf 7 may be made of any suitable flexible, temperature controlling, and breathable material to provide comfort and support to the user. This functionality is similar to a traditional turtle neck constriction for sweaters and other cold weather garments. The scarf 7 may have the option to affix indicia such as user's name 6D and/or number insignia 6B, 6C on the scarf 7 itself to better identify user in the event that the user is a participant or player during an athletic activity. The scarf 7 may be affixed to the two shoulder straps 1A, 1B via a series of attachment devices, such as buttons 8A, 8B, 8C, 8D, 8E, 8F, 8G, 8H or snaps. In one embodiment, the female portion of a button 8E, 8F, 8G, 8H may be affixed to the scarf 7 while the male portion of the button 8A, 8B, 8C, 8D may be affixed to the two shoulder straps 1A, 1B proximate the end of the shoulder straps 1A, 1B closest to the scarf 7 (i.e. medial ends), but an alternative version may reverse that male/female designation for buttons 8A, 8B, 8C, 8D, 8E, 8F, 8G, 8H. Further, it is envisioned that alternative methods of connection will be offered by the present invention, including but not limited to sewing the scarf 7 directly to the shoulder straps 1A, 1B or utilizing a zipper mechanism, VELCRO, snaps, hooks, nylon strapping, or any other suitable attachment devices.

The shoulder straps 1A, 1B and front harness straps 2A, 2B, 3A, 3B, 4A, 4B may be constructed from compression fabric or material similar to that sold under the trademark HYPERCOOL® by Nike, Inc. or a similar alternative in varies embodiments. The individual shoulder harness straps 1A, 1B and front harness straps 2A, 2B, 3A, 3B, 4A, 4B may be sewn together with industrial strength thread to provide support and to compensate for the strain of the user during an athletic activity. According to one embodiment, the shoulder straps 1A, 1B, front upper compression straps 3A, 3B, and front lower compression straps 4A, 4B may be approximately 1.5 inch wide, but it should be clearly understood that the shoulder straps 1A, 1B, front upper compression straps 3A, 3B, and front lower compression straps 4A, 4B may vary in width depending on the size or the participant and the size of the harness 100. It is envisioned that the present invention will be offered in multiple sizes from x-small to xxx-large. Furthermore, in one embodiment, the front lateral support straps 2A, 2B may be approximately 1.0 inch wide, but it should be clearly understood that the lateral support straps may vary in width depending on the size or the participant and the size of the harness 100.

The front patch 5A may display a user's/player's indicia 6A (which may be a name, number, logo, insignia, number or any other suitable identifier) on the front of the harness 100. The front patch 5A may be connected to the medial ends of the front upper compression straps 3A, 3B, and front lower compression straps 4A, 4B. The player indicia 6A may be imprinted, etched, or embroidered on the front patch 5A. The front patch 5A may be adapted to be positioned over a center of the chest of the user. The front patch 5A may be made of a solid material coupled to the medial ends of the front upper compression straps 3A, 3B and front lower compression straps 4A, 4B or made of a fabric that may be sewn to the medial ends of the front upper compression straps 3A, 3B and front lower compression straps 4A, 4B. In another embodiment, front right upper compression strap 3A and front left lower compression strap 4B may be constructed as a single continuous strap and the front left upper compression strap 3B and front right lower compression strap 4A may also be constructed as a single continuous strap, wherein both continuous straps intersect at the center of the chest of the user and continue uncut underneath the front patch 5A. In one embodiment, the front patch 5A may be a three 3.0 inch diameter octagon, but it should be clearly understood that substantial benefit may be derived from the patch having an alternative suitable size. It should also be clearly understood that the patch 5A shape may be of any shape (e.g. a circle, square, etc.) depending on the design variation of the various teams and players that the user may be a part of.

Figure 3:
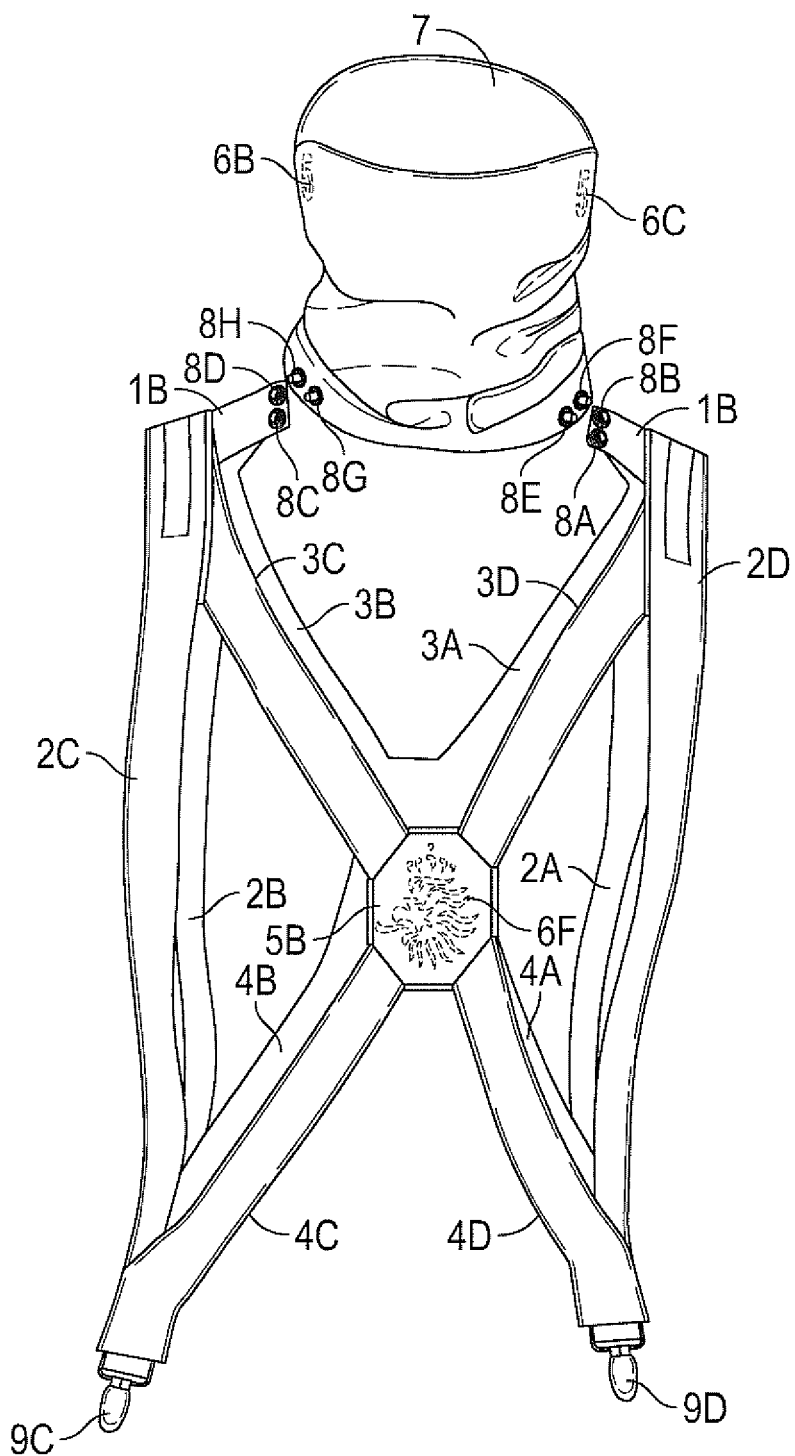
FIG. 3 is a back view of the garment of the present invention depicting the layout and articulation of the harness straps placement and location. Additionally, this figure depicts the location of team insignias or sponsor logo, and the location of the head and neck covering articulation to the harness via a connection method.
Figure 4:
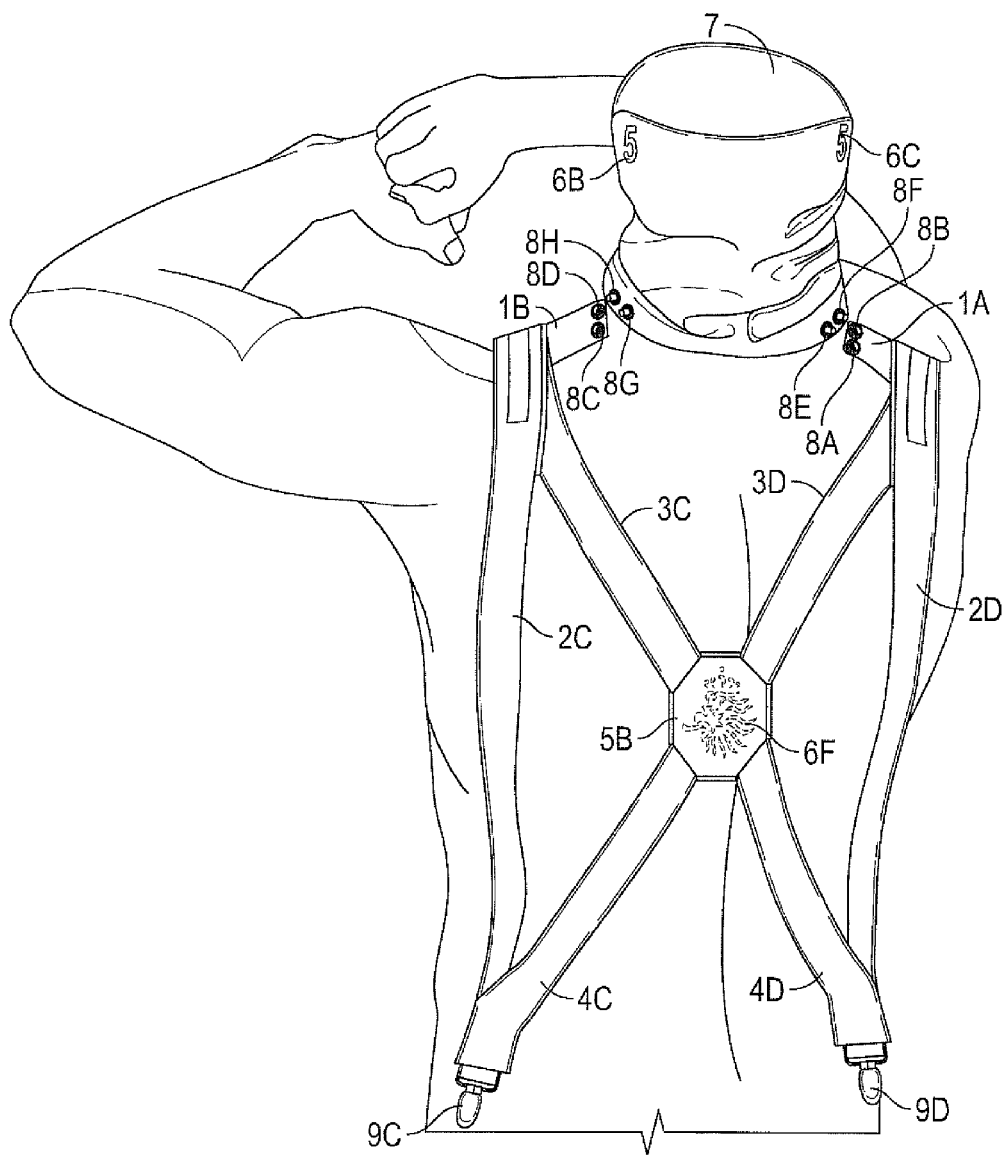
FIG. 4 is a back view of the garment of FIG. 3, shown as worn by a user.

FIGS. 3-4 each show a back view of the harness 100 of the present invention depicting the layout and articulation of the shoulder harness straps 1A, 1B and rear harness straps 2C, 2D, 3C, 3D, 4C, 4D placement and location. The rear harness straps may comprise: a rear left upper compression strap portion 3C; a rear right upper compression strap portion 3D; a rear left lower compression strap portion 4C; a rear right lower compression strap portion 4D; a rear left lateral support strap 2C and a rear right lateral support strap 2D. The rear right upper compression strap 3D may be coupled at one end to the lateral end of the right shoulder strap 1A, extend across a portion of the upper torso of the user, and be coupled at another end to a rear patch 5B. The rear left lower compression strap 4C may be coupled at one end to the rear patch 5B, extend across the remaining portion of the upper torso of the user, and be coupled at another end to a distal end of the rear left lateral support strap 2C. The rear left upper compression strap 3C may be coupled at one end to the lateral end of the left shoulder strap 1B, extend across a portion of the upper torso of the user, and be coupled at another end to the rear patch 5B. The rear right lower compression strap 4D may be coupled at one end to the rear patch 5B, extend across the remaining portion of the upper torso of the user, and be coupled at another end to a distal end of the rear right lateral support strap 2D.

Similar to the front of the harness 100, the back of the harness 100 may have a rear patch 5B that displays a player's indicia 6F, (which may be a name, number, logo, insignia, number or any other suitable identifier). The rear patch 5B may be adapted to be positioned over a center of the back of the user. The rear patch 5B may connected to the medial ends of the rear upper compression straps 3C, 3D and rear lower compression straps 4C, 4D. The player indicia 6F may be imprinted, etched, or embroidered on the rear patch 5B. The rear patch 5B may be made of a solid material coupled to the medial ends of the rear upper compression straps 3C, 3D and rear lower compression straps 4C, 4D or made of fabric that may be sewn to the medial ends of the rear upper compression straps 3C, 3D and the rear lower compression straps 4C, 4D. In another embodiment, rear left upper compression strap 3C and rear right lower compression strap 4D may be constructed as a single continuous strap and rear right upper compression strap 3D and rear left lower compression strap 4C may also be constructed as a single continuous strap, wherein both continuous straps intersect at the center of the back of the user and continue uncut underneath the rear patch 5B. The rear patch 5B may have the same dimensions and/or shape of the front patch 5A to match. For example, the rear patch 5B may also be shaped like an octagon, providing a plurality of flat edges to which the rear left upper compression strap 3C, rear right lower compression strap 4D, rear right upper compression strap 3D, and rear left lower compression strap 4C may attach. Also, the material used to make the rear harness straps 2C, 2D, 3C, 3D, 4C, 4D and the widths of the rear harness straps 2C, 2D, 3C, 3D, 4C, 4D may be the same as the material and widths of the corresponding front harness straps 2A, 2B, 3A, 3B, 4A, 4B. Additionally, this embodiment follows the detailed description of FIG. 1 in relation to the connection of the scarf 7 to the harness 100, sewing methods of the rear harness straps 2C, 2D, 3C, 3D, 4C, 4D and connections of the rear patch 5B bearing the player's indicia 6F.

Figure 5:
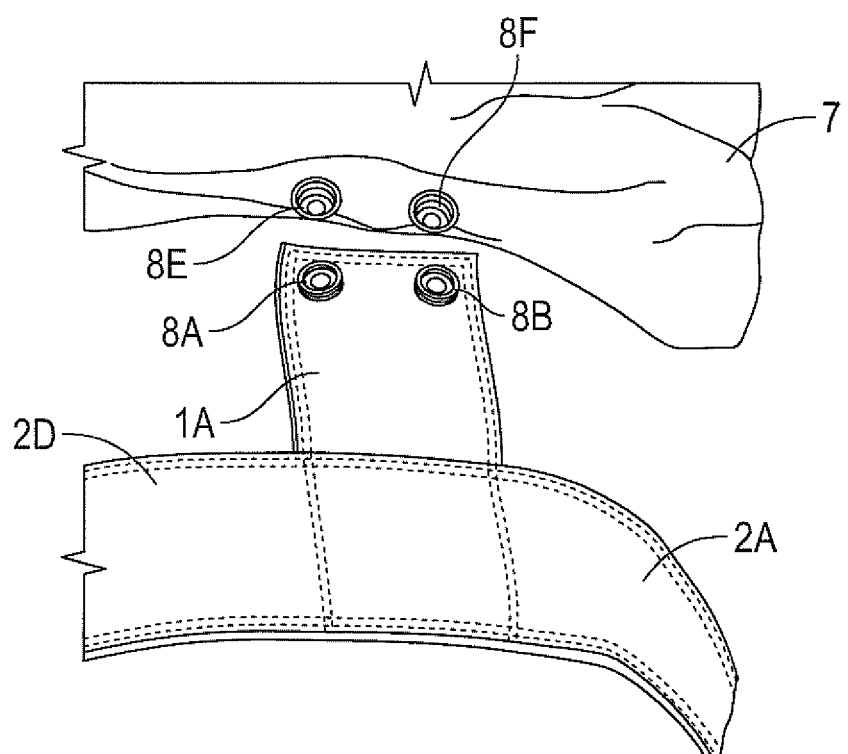
FIG. 5 is a side view of the garment of the present invention focused on the shoulder area of the present invention, depicting the layout and articulation of the harness straps at the shoulder area. Additionally, this figure depicts one option or embodiment of the articulation of the head and neck covering to the harness.
Figure 6:
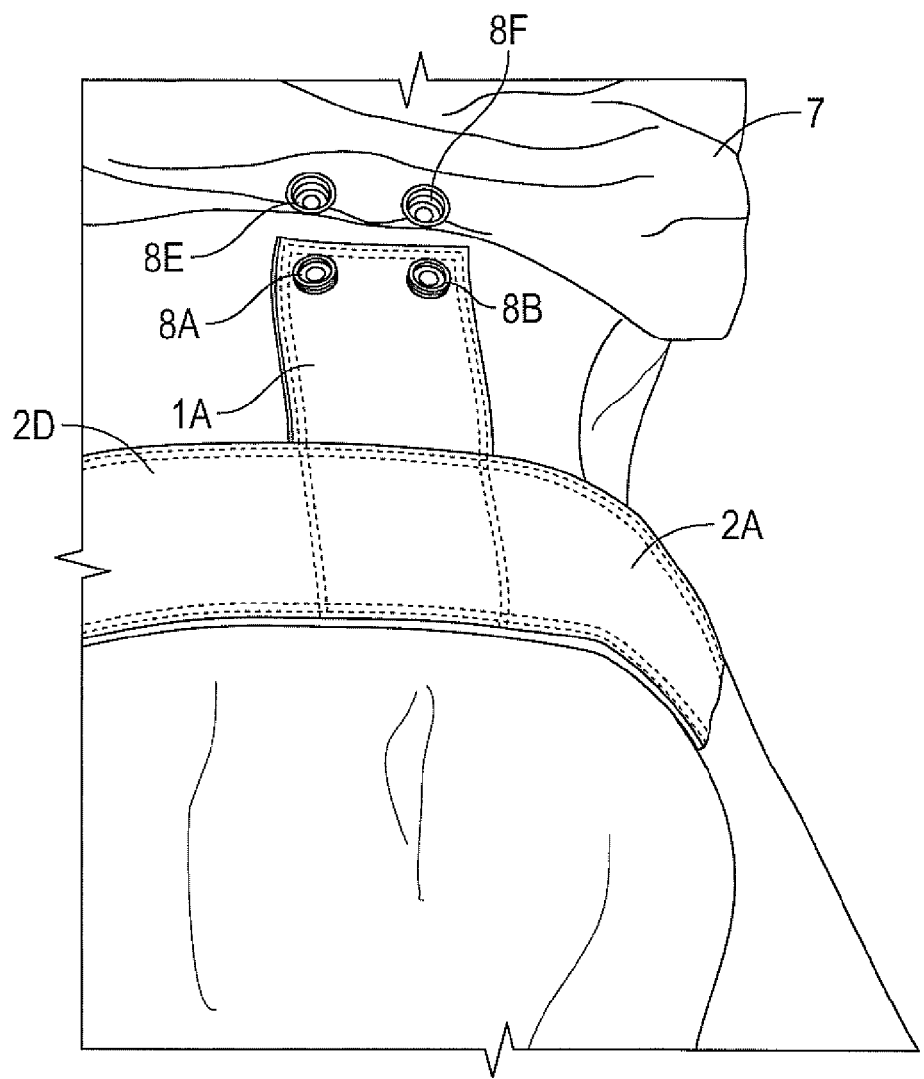
FIG. 6 is a side view of the garment of FIG. 5, shown as worn by a user.

FIGS. 5-6 show a side view of the present invention focused on the shoulder area of the present invention, depicting the layout and articulation of the right shoulder strap 1A, the front right lateral support strap 2A, and the rear right lateral support strap 2D at the right side shoulder area. The structure of the harness 100 on the left side of the shoulder would be a mirror image of the right shoulder should in these figures. In this embodiment, the scarf 7 may connect to the medial ends of the shoulder straps 1A, 1B via a plurality of buttons 8A, 8B, 8E, 8F. As shown, one or more male button portions 8A, 8B may be coupled to the medial end of the shoulder strap 1A while the corresponding female button portions 8E, 8F may be coupled to a bottom edge of the scarf 7. It should be clearly understood that the male button portions 8A, 8B and female button portions 8E, 8F may be reversed. A similar configuration of male button portions 8C, 8D and female button portions 8G, 8H will also appear on the opposite side of the harness 100 at the left shoulder strap 1B and scarf 7. Additional detail is depicted on the enforced sewing methods of the harness straps in these figures.

Figure 7:
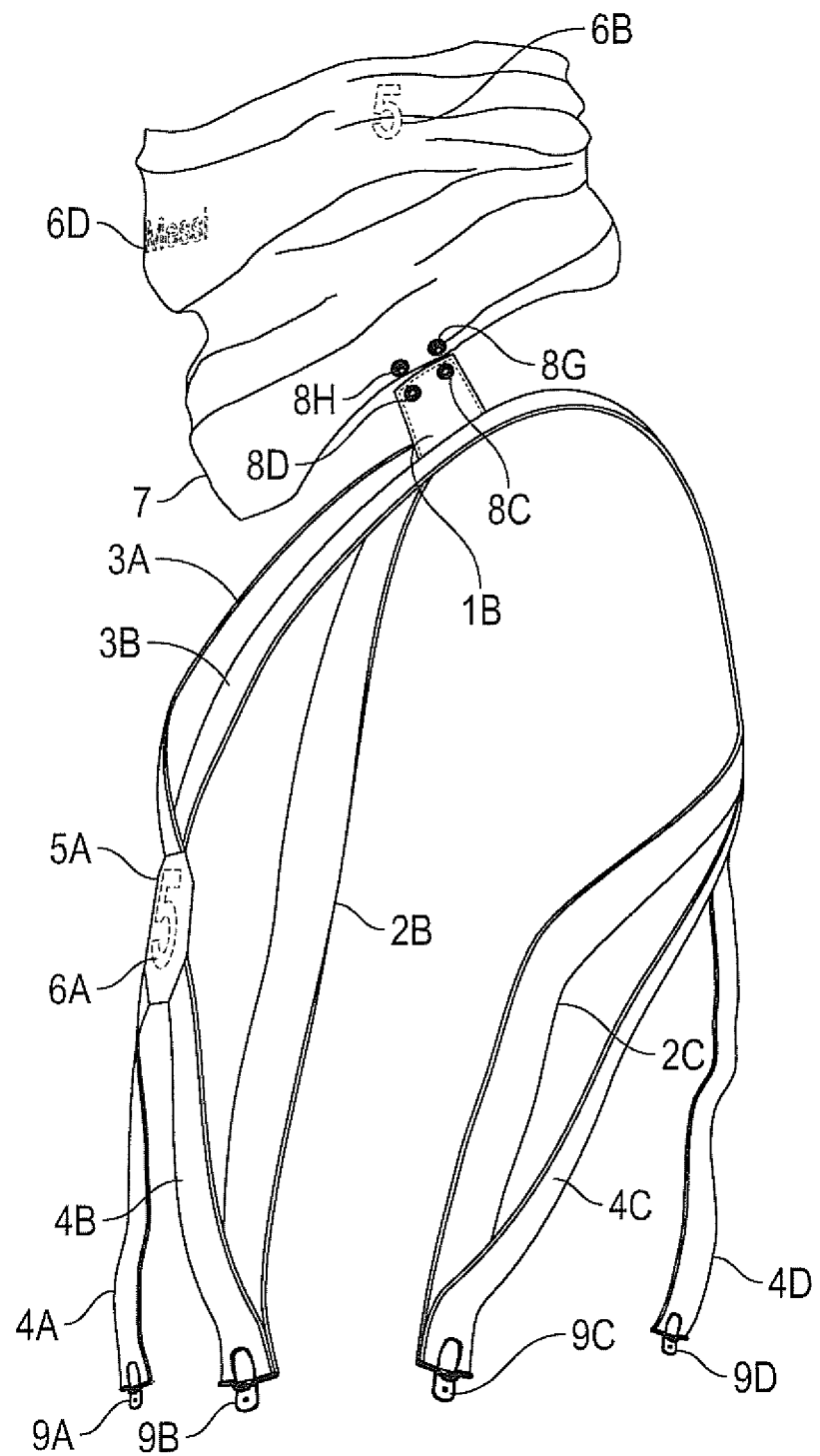
FIG. 7 is a side view of the garment of the present invention depicting the layout and articulation of the harness straps placement and location. Additionally, this figure depicts the location of number insignias for the athletic participant, a potential sponsor logo, and the location of the head and neck covering articulation to the harness via a connection method.
Figure 8:
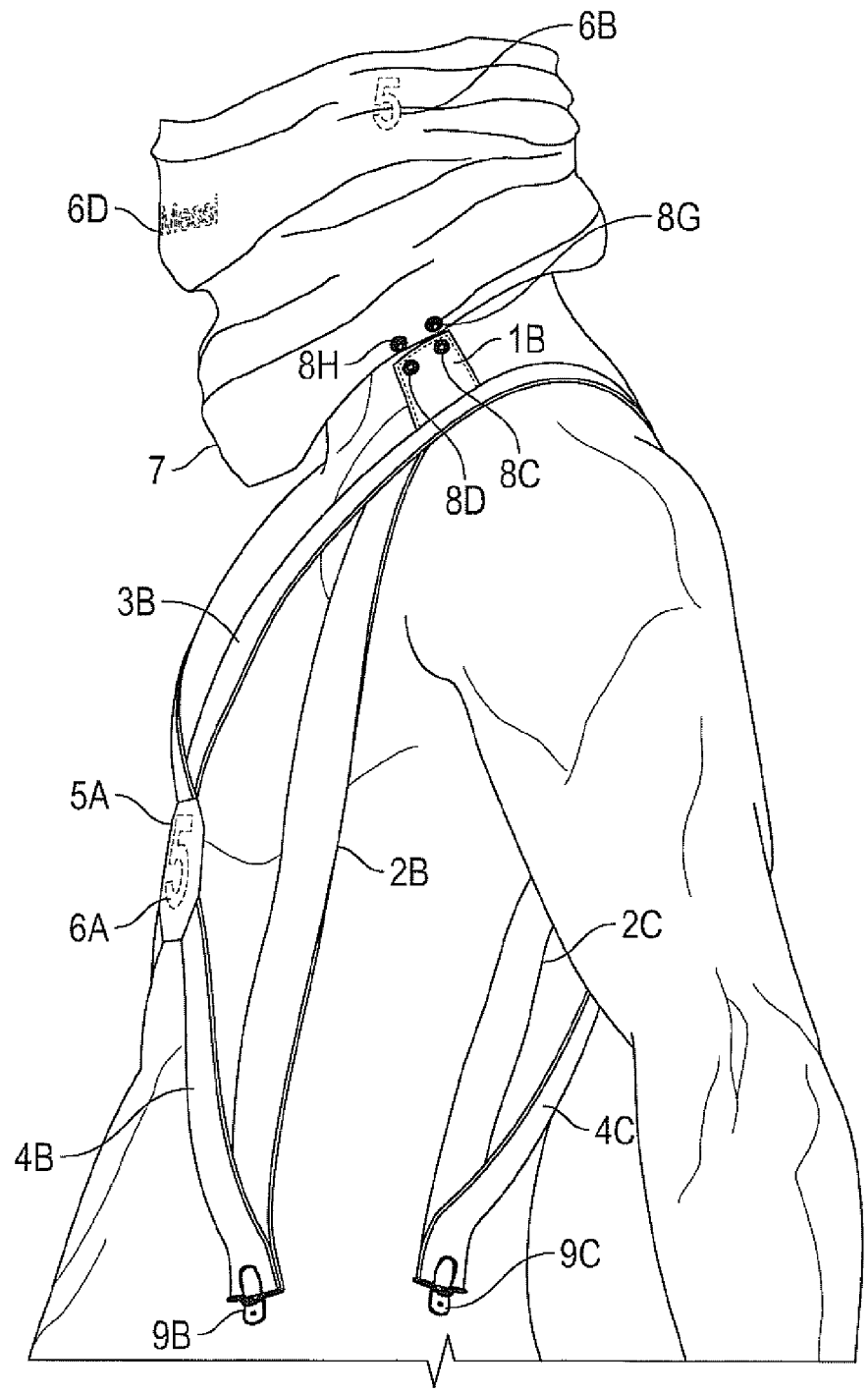
FIG. 8 is a side view of the garment of FIG. 7, shown as worn by a user.

FIGS. 7-8 show a side view of the present invention depicting the layout and articulation of the left shoulder strap 1B, front left lateral support strap 2B, front left upper compression strap 3B, and front left lower compression strap 4B. A plurality of clasps 9A, 9B, 9C, 9D may be used to couple the harness 100 to certain garments worn by the user. For example, a front right pin clasp 9A may be coupled to the lateral end of the front right lower compression strap 4A and/or to the distal end of the front right lateral support strap 2A; a front left pin clasp 9B may be coupled to the lateral end of the front left lower compression strap 4B and/or to the distal end of the front left lateral support strap 2B; a rear left pin clasp 9C may be coupled to the lateral end of the rear left lower compression strap 4C and/or to the distal end of the rear left lateral support strap 2C; and a rear right pin clasp 9D may be coupled to the lateral end of the rear right lower compression strap 4D and/or to the distal end of the rear right lateral support strap 2D.

Figure 9:
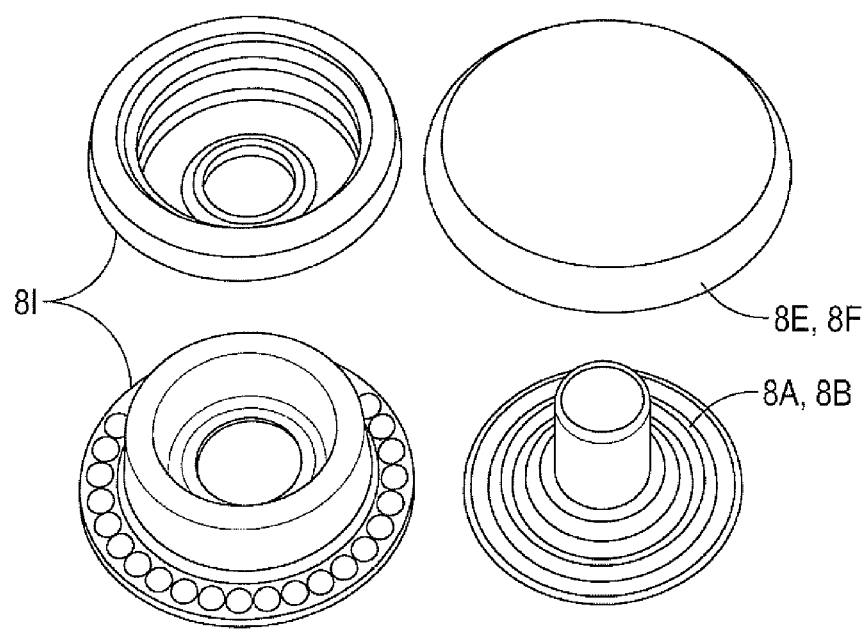
FIG. 9 is a top-down focused look of one potential embodiment of the articulation mechanism of the neck and facial covering to the harness at the shoulder location. This specific embodiment that is considered pertains to buttons that use grommets to secure the button to the harness and the scarf fabric respectively.

FIG. 9 is a top-down focused look of one potential embodiment of the articulation mechanism of the neck and facial covering to the harness 100 at the shoulder location. This specific embodiment that is considered pertains to buttons 8A, 8B, 8C, 8D, 8E, 8F, 8G, 8H that use grommets 8I to secure the button 8A, 8B, 8C, 8D to the shoulder straps 1A, 1B and secure the corresponding buttons 8E, 8F, 8G, 8H to the scarf 7 fabric. The common buttons 8A, 8B, 8C, 8D, 8E, 8F, 8G, 8H of this embodiment are not considered as a critical element of the present invention and all rights specifically to the buttons 8A, 8B, 8C, 8D, 8E, 8F, 8G, 8H are waived in favor of public domain usage. This embodiment displays the use of common buttons 8A, 8B, 8C, 8D, 8E, 8F, 8G, 8H, but varied embodiments of the present invention consider sewing method of attachment, VELCRO attachment, or even an embodiment with a zipper attachment for the scarf 7 to the shoulder straps 1A, 1B. Regardless of the methodology of attachment, the scarf 7 shall articulate with the shoulder straps 1A, 1B of the harness 100 to provide support and warmth without the concern for movement out of place to distract the participant.

Figure 10:
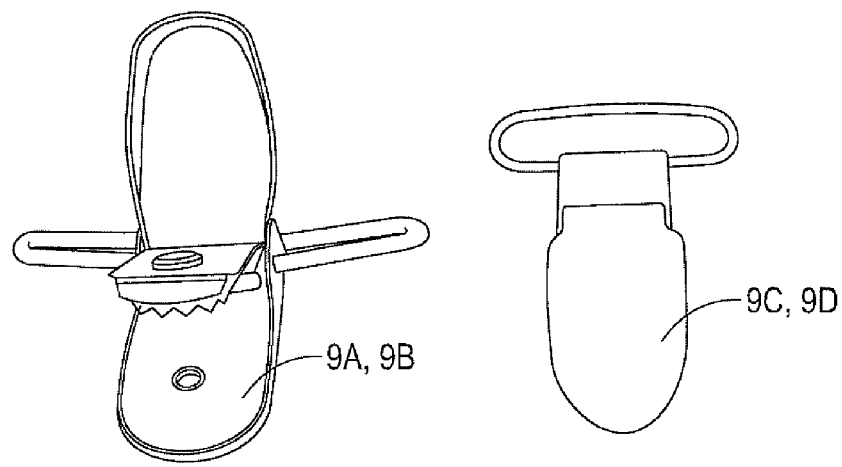
FIG. 10 is a perspective view of an example of a clasp mechanism that may be used to couple the harness to certain articles of the user's clothing in order to hold the harness in place.

FIG. 10 is a perspective view of a clasp mechanism 9A, 9B, 9C, 9D that may be used to couple the harness 100 to certain garments worn by the user. For example, the clasps 9A, 9B, 9C, 9D may be coupled to a waist band of pants/shorts worn by the user. This will help to keep the harness 100 in place and to prevent the harness 100 from riding upwardly on the user. The clasps 9A, 9B, 9C, 9D may be made of metal, plastic, carbon fiber, or any other suitable material.

Figure 11:
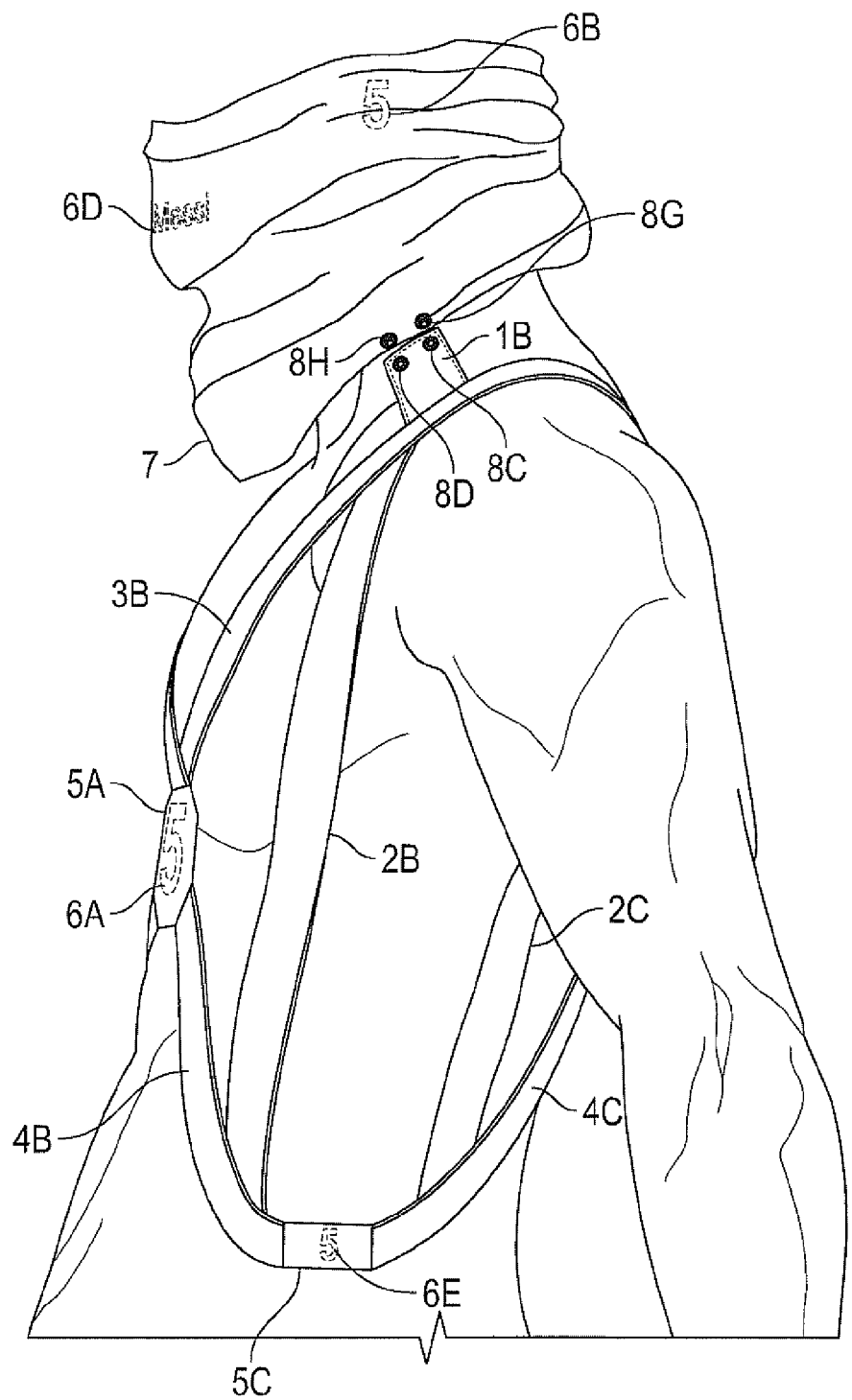
FIG. 11 is a side view of an alternative embodiment of the garment of the present invention, shown as worn by a user.

FIG. 11 shows an alternative embodiment wherein the harness 100 may have a side patch 5C on one or both sides of the harness 100. For example, a left side patch 5C may be coupled to the lateral ends of the front left lower compression strap 4B and the rear left lower compression strap 4C and a right side patch 5C may be coupled to the lateral ends of the front right lower compression strap 4A and the rear right lower compression strap 4D. The side patch 5C may bear a player indicia 6E thereon (which may be a name, number, logo, insignia, number or any other suitable identifier). The player indicia 6E may be imprinted, etched, or embroidered on the side patch 5C. One side patch 5C may be made of a solid material coupled to the lateral ends of the lower compression straps 4B to 4C (on the left side) and another side patch 5C may be coupled to the lateral ends of the lower compression straps 4A to 4D (on the right side). Alternatively, the side patches 5C may be made of fabric that may be sewn to the lateral ends of the lower compression straps 4B, 4C (on the left side) and to the lateral ends of the lower compression straps 4A, 4D (on the right side).

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A garment comprising:
    a harness adapted to be positioned around an upper torso of a user, wherein the harness comprises:
        a left shoulder strap;
        a right shoulder strap;
        a front left lateral support strap and a rear left lateral support strap coupled to and extending downwardly from the left shoulder strap;
        a front right lateral support strap and a rear right lateral support strap coupled to and extending downwardly from the right shoulder strap;
        a front left compression strap and a rear left compression strap coupled to and extending diagonally and downwardly from the left shoulder strap, wherein the front left compression strap is adapted to extend across the upper torso of the user and couple to the front right lateral support strap and wherein the rear left compression strap is adapted to extend across the upper torso of the user and couple to the rear right lateral support strap;
        a front right compression strap and a rear right compression strap coupled to and extending diagonally and downwardly from the right shoulder strap, wherein the front right compression strap is adapted to extend across the upper torso of the user and couple to the front left lateral support strap and wherein the rear right compression strap is adapted to extend across the upper torso of the user and couple to the rear left lateral support strap; and
        a front patch coupled to the front left compression strap and to the front right compression strap, wherein the front patch bears at least one indicia that is adapted to identify the user; and
    a neck covering removably coupled to the harness, wherein the neck covering has an open bottom and an open top and is adapted to receive a head of the user therethrough.

2. The garment of claim 1 further comprising a rear patch coupled to the rear left compression strap and to the rear right compression strap, wherein the rear patch bears at least one indicia that is adapted to identify the user.

3. The garment of claim 2 wherein the rear right compression strap and the rear left compression strap each comprises:

an upper portion that is coupled at one end to a shoulder strap adapted to be positioned on one side of the upper torso of the user, is adapted to extend across a portion of the upper torso of the user, and is coupled at an opposite end to the rear patch; and a lower portion that is coupled at one end to the rear patch, is adapted to extend across a remainder of the upper torso of the user, and is coupled at an opposite end to a lateral support strap adapted to be positioned on an opposite side of the user.

4. The garment of claim 1 wherein a bottom portion of the neck covering is coupled to the left shoulder strap and to the right shoulder strap by a at least one of a button, a hook, a snap, a zipper, and a hook and loop fastener.

5. The garment of claim 4 further comprising:
at least two button portions coupled to a medial end of the left shoulder strap;
at least two corresponding button portions coupled to the bottom portion of the neck covering and adapted to engage the at least two button portions coupled to the medial end of the left shoulder strap;
at least two button portions coupled to a medial end of the right shoulder strap; and
at least two corresponding button portions coupled to the bottom portion of the neck covering and adapted to engage the at least two button portions coupled to the medial end of the right shoulder strap.

6. The garment of claim 1 wherein the front right compression strap and the front left compression strap each comprises:
an upper portion that is coupled at one end to a shoulder strap adapted to be positioned on one side of the upper torso of the user, is adapted to extend across a portion of the upper torso of the user, and is coupled at an opposite end to the front patch; and
a lower portion that is coupled at one end to the front patch, is adapted to extend across a remainder of the upper torso of the user, and is coupled at an opposite end to a lateral support strap adapted to be positioned on an opposite side of the user.

7. The garment of claim 1 further comprising a left side patch coupled at one end to a lateral end of the front left compression strap and coupled at an opposite end to a lateral end of the rear left compression strap, wherein the left side patch bears at least one indicia that is adapted to identify the user.

8. The garment of claim 1 further comprising a right side patch coupled at one end to a lateral end of the front right compression strap and coupled at an opposite end to a lateral end of the rear right compression strap, wherein the right side patch bears at least one indicia that is adapted to identify the user.

9. The garment of claim 1 wherein the harness is made of compression fabric.

10. The garment of claim 1 further comprising a plurality of clasps, wherein one clasp is coupled to and extends downwardly from each of the front left lateral support strap, the front right lateral support strap, the rear left lateral support strap, and the rear right lateral support strap and wherein the clasps are adapted to removably couple the harness to a waist band of another article of clothing of the user in order to prevent the harness from riding upwardly.

11. An athletic garment comprising:
a harness adapted to be positioned around an upper torso of a user, wherein the harness comprises:
a left shoulder strap;
a right shoulder strap;
a front left lateral support strap and a rear left lateral support strap coupled to and extending downwardly from a lateral end of the left shoulder strap;
a front right lateral support strap and a rear right lateral support strap coupled to and extending downwardly from a lateral end of the right shoulder strap;
a front patch adapted to be positioned over a center of a chest of the user, wherein the front patch bears at least one indicia that is adapted to identify the user;
a rear patch adapted to be positioned over a center of a back of the user, wherein the rear patch bears at least one indicia that is adapted to identify the user;
a front left upper compression strap coupled at one end to the lateral end of the left shoulder strap and coupled at an opposite end to the front patch;
a front right lower compression strap coupled at one end to the front patch and coupled at an opposite end to a distal end of the front right lateral support strap;
a front right upper compression strap coupled at one end to the right shoulder strap and coupled at an opposite end to the front patch;
a front left lower compression strap coupled at one end to the front patch and coupled at an opposite end to the front left lateral support strap;
a rear left upper compression strap coupled at one end to the left shoulder strap and coupled at an opposite end to the rear patch;
a rear right lower compression strap coupled at one end to the rear patch and coupled at an opposite end to the rear right lateral support strap;
a rear right upper compression strap coupled at one end to the right shoulder strap and coupled at an opposite end to the rear patch; and
a rear left lower compression strap coupled at one end to the rear patch and coupled at an opposite end to the rear left lateral support strap; and
a neck covering removably coupled to the harness, wherein the neck covering has an open bottom and an open top and is adapted to receive a head of the user therethrough, and wherein the neck covering bears at least one indicia that is adapted to identify the user; and
a plurality of clasps, wherein one clasp is coupled to and extends downwardly from each of front left lateral support strap, the front right lateral support strap, the rear left lateral support strap, and the rear right lateral support strap and wherein the clasps are adapted to removably couple the harness to another article of clothing of the user; and
wherein the harness defines a plurality of open areas in the garment.

* * * * *